(12) United States Patent
Aven

(10) Patent No.: US 6,383,984 B1
(45) Date of Patent: May 7, 2002

(54) AQUEOUS SUSPENSION CONCENTRATE

(75) Inventor: Michael Aven, Mainz (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/484,563

(22) Filed: Jan. 18, 2000

Related U.S. Application Data
(60) Provisional application No. 60/117,708, filed on Jan. 29, 1999.

(51) Int. Cl.$^7$ ................................. A01N 57/12
(52) U.S. Cl. .................. 504/116.1; 568/333; 504/348
(58) Field of Search ................ 568/420, 333; 514/686; 504/116

(56) References Cited

U.S. PATENT DOCUMENTS

| | | | |
|---|---|---|---|
| 5,294,597 A | 3/1994 | Foster et al. | |
| 5,332,714 A | 7/1994 | Albrecht et al. | ............. 504/116 |
| 5,444,078 A | 8/1995 | Yu et al. | ..................... 514/732 |
| 5,679,866 A | 10/1997 | Curtze et al. | |
| 5,773,663 A | 6/1998 | Curtze et al. | ................ 568/333 |
| 5,922,905 A | 7/1999 | Curtze et al. | ................ 562/474 |
| 5,945,567 A | 8/1999 | Curtze et al. | ................ 568/333 |
| 6,001,883 A | * 12/1999 | Curtze et al. | ................ 514/687 |

FOREIGN PATENT DOCUMENTS

| | | | |
|---|---|---|---|
| EP | 0 407 874 | 7/1990 | |
| GB | 2113092 | 8/1983 | .......... A01N/25/02 |
| JP | 7033606 | 2/1995 | .......... A01N/25/04 |
| WO | WO 96/20203 | 7/1996 | |

OTHER PUBLICATIONS

Hoorne et al, Novel adjuvants for agrochemical formulations based on sugar ethers, AN 1994:2782, 1993.*

Nabeya et al, Pesticides applicable to the surface of water, AN 1995:519023, 1995.*

Albrecht et al, Perfluoroalkyl phosphonate and phosphinate defoaming agents for pesticide formulations, AN 1991:508588, 1991.*

Alkyl Polyglycosides, Edited by K. Hill, W. v Rybinski, G. Stoll, VCH Weinheim, New York, Basel Cambridge, Tokyo 1997, pp. 10, 20, 1331–1337.

D. Hoorne et al., "Novel Adjuvants For Agrochemical Formulations Based on Sugar Ethers", ASTM, 04–011460–8, Pesticide Formulations and Application Systems: 12$^{th}$ vol. Feb. 9, 1993, pp. 3–21.

* cited by examiner

Primary Examiner—Deborah D. Carr
(74) Attorney, Agent, or Firm—Charles F. Costello

(57) ABSTRACT

The invention relates to an aqueous, concentrated suspension (SC) for crop protection active compounds which comprises (a) 50 to 400 g/L of at least one crop protection active compound;

(b) 50 to 500 g/L of at least one adjuvant, which reduces the surface tension in the spray dilution 40 mN/m or less and does not promote the particle growth of the crop protection active compound;

(c) at least one surfactant selected from the groups (c1) and (c2):
  (c1) 5 to 75 g/L of one or more non-ionic dispersants,
  (c2) 10 to 100 g/L of one or more anionic dispersants, (d) up to 150 g/L of one or more anti-freezing agents, (e) up to 25 g/L of one or more defoamers, (f) up to 25 g/L of one or more preservatives, and (g) 200 to 800 g/L of water, wherein the adjuvant (b) is selected from the group consisting of amine alkoxylates, polyoxyalkylene triglycerides, alkylpolyglycosides, alkenyl succinic anhydride derivatives, polyvinylpyrrolidones, perfluoroalkyl acids derivatives, and mixtures thereof;

and to the use of such a concentrate suspension as a pesticide.

12 Claims, No Drawings

US 6,383,984 B1

AQUEOUS SUSPENSION CONCENTRATE

This application claims priority from copending provisional application(s) serial No. 60/117,708 filed on Jan. 29, 1999.

BACKGROUND OF THE INVENTION

This invention concerns an aqueous, storage stable suspension concentrate (SC) for crop protection active compounds, a method for the manufacture of such suspensions, and their use for combating pests.

As a rule inert ingredients must be used to bring crop protection active compounds, for example fungicidal compounds, into such a form that the user can apply them either as such or after dilution with water. The correct choice of suitable inert ingredients for the formulation often determines to a significant extent whether the active ingredient can display its full efficacy after application. When selecting suitable ingredients to insure the physicochemical stability of the formulation, it must be taken into account that not every active ingredient can be processed into any given formulation type without losses in stability and/or efficacy.

The efficacy of the active components can often be improved by addition of other ingredients such as adjuvants. An adjuvant is defined here as a substance which can increase the biological activity of an active ingredient but is not itself significantly biologically active. The adjuvant can either be included in the formulation or can be added to the spray tank together with the formulation containing the active ingredient. In view of an easy and safe handling and dosing of these adjuvants by the end-user and in view of avoiding unnecessary packing material, it is desirable to develop concentrated formulations which already contain such adjuvants.

SUMMARY OF THE INVENTION

The present invention relates to an aqueous, concentrated suspension (SC) for crop protection active compounds which comprises (a) 50 to 400 g/L of at least one crop protection active compound;

(b) 50 to 500 g/L of at least one adjuvant, which has the capability of reducing the surface tension in the spray dilution to 40 mN/m or lower and does not significantly promote the particle growth of the crop protection active compound in the stored SC;

(c) at least one surfactant selected from the groups (c1) and (c2):

(c1) 5 to 75 g/L of one or more non-ionic dispersants, and (c2) 10 to 100 g/L of one or more anionic dispersants, (d) up to 150 g/l of one or more anti-freezing agents, (e) up to 25 g/L of one or more defoamers, (f) up to 25 g/L of one or more preservative, and (g) 200 to 800 g/L of water, wherein the adjuvant (b) is selected from the group consisting of amine alkoxylates, polyoxyalkylene triglycerides, alkylpolyglycosides, alkenyl succinic anhydride derivatives, polyvinylpyrrolidones, perfluoroalkyl acids derivatives, mixtures thereof and mixtures with diluents. Another aspect of the present invention is a process for the preparation of such a SC which comprises (1) air-milling of 50 to 400 g/L of one or more crop protection active compounds (a) optionally in the presence of one or more anionic dispersants (c2), and/or a milling aid such as kaolin or silica, and (2) mixing all the components (a) to (g) in a dissolver.

Furthermore, the invention relates to a method for the control of pests at a locus which comprises diluting a SC according to the invention with water and treating the said locus with the obtained diluted formulation.

Those and other objects and features of the invention will become more apparent from the detailed description set forth hereinbelow.

DETAILED DESCRIPTION OF THE PREFERRED EMBODIMENTS

It has now been found that, surprisingly, stable aqueous SC formulation comprising one or more crop protection active compounds (a) and one or more adjuvants (b) in combination with one or more non-ionic dispersants (c1) and/or one or more anionic dispersants (c2) and can be prepared.

The biological activity of the active ingredients (a) can be increased by including the adjuvants (b) in the spray dilution or directly in the formulation. However, according to the present invention the adjuvants (b) are incorporated into the concentrated formulation.

The term pests as used hereinabove and hereinbelow includes but is not limited to plant pathogens, insects and weeds.

In principle all crop protection active compounds can be used for the non-aqueous concentrated suspensions according to the invention. However, solid crop protection active compounds are preferred.

As a rule solid crop protection active compounds are used which have a low solubility in water. A solubility of less than 10 g/L, in particular less than 5 g/L in water is preferred.

The compositions of this invention can be applied to the plants or their environment with other active substances. These active substances (a) can be either fertilizers or agents which donate trace elements or other preparations which influence plant growth. However, they can also be selective herbicides, insecticides, fungicides, bactericides, nematicides, algicides, molluscicides, rodenticides, virucides, compounds inducing resistance into plants, biological control agents such as viruses, bacteria, nematodes, fungi and other microorganisms, repellents of birds and animals, and plant growth regulators, or mixtures of several of these preparations.

The active ingredients, which are provided in the form of the aqueous SC formulation according to the invention, include all suitable biologically active compounds for plant protection, preferably fungicides, herbicides, insecticides, acaricides, nematicides and repellents, in particular fungicides. Active ingredients which are solid at room temperature are preferred, in particular those with a melting point of higher than 50° C.

Mixtures of different biologically active compounds can have a broader spectrum of activity than a single compound alone. Furthermore, these can exhibit a synergistic effect compared with the single active ingredients. In a preferred embodiment, the formulation of the present invention can be used with a mixture of active ingredients, in the case of mixtures one of the active ingredients can be dissolved in the continuous phase of the SC formulation according to the invention.

Preferred fungicides for use in the compositions of the present invention are the commercially available compounds selected from the group consisting of:

AC 382042, anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenamidone, fenarimol, fenbuconazole, fenfuram, fenhexamid, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, IKF-916, imazalil, iminoctadine, ipconazole, iprodione, isoprothiolane, iprovalicarb, kasugamycin, KH-7281, kitazin P, kresoxim-methyl, mancozeb, maneb, mepanipyrim, mepronil, metalaxyl, metconazole, methfuroxam, MON 65500, myclobutanil, neoasozin, nickel dimethyidithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidone, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanid, triadimefon, triadimenol, triazbutil, triazoxide, tricyclazole, tridemorph, trifloxystrobin, triflumizole, triforine, triticonazole, validamycin A, vinclozolin, XRD-563, zarilamid, zineb, ziram.

In addition, the formulations according to the invention may contain at least one compound of the following classes of biological control agents such as viruses, bacteria, nematodes, fungi, and other microorganisms which are suitable for the control of insects, weeds or plant diseases, or to induce host resistance in the plants. Examples of such biological control agents are: *Bacillus thuringiensis, Verticillium lecanii, Autographica californica* NPV, *Beauvaria bassiana, Ampelomyces quisqualis, Bacilis subtilis, Pseudomonas fluorescens, Steptomyces griseoviridis* and *Trichoderma harzianum.*

Moreover, the formulations according to the invention may contain at least one chemical agent that induces the systemic acquired resistance in plants such as, for example, isonicotinic acid or derivatives thereof, 2,2-dichloro-3,3-dimethylcylopropylcarboxylic acid or BION.

Also preferred compositions can include derivatives of benzoylbenzenes which are disclosed, for example, by European Patent Applications EP 0 727 141, in particular the compounds of formula I

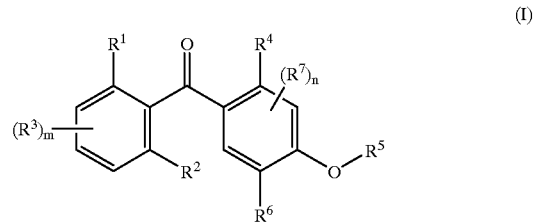

wherein
$R^1$ represents a halogen atom, an optionally substituted alkyl, alkanoyloxy or alkoxy group; or a hydroxy group,
$R^2$ represents a halogen atom, an optionally substituted alkyl group,
$R^3$ represents a halogen atom or an optionally substituted alkyl group,
m is 0 or an integer of 1 to 3;
$R^4$ independently represents a halogen atom, an optionally substituted alkyl or alkoxy group or a nitro group;
$R^5$ represents an optionally substituted alkyl group;
$R^6$ represents a halogen atom, a cyano, carboxy, hydroxy or nitro group or an optionally substituted alkyl, alkoxy, alkenyl, alkylthio, alkylsulphinyl, alkylsulphonyl or amino group;
$R^7$ represents a halogen atom or a nitro group, an optionally substituted alkyl, alkoxy, alkenyloxy, alkynyloxy, alkylthio, cycloalkyl, cycloalkyloxy, aryloxy group; and
n is 0, 1 or 2.

Preferred are those compounds of formula I wherein $R^1$ represents a, chlorine atom or a methyl, methoxy or a hydroxy group and $R^2$ represents a chlorine atom or a methyl group; $R^3$ represents a halogen atom; $R^4$ and $R^5$ each represents a methyl group; and $R^6$ and $R^7$ each represent a $C_{1-6}$ alkoxy or a benzyloxy group; m is 0 or 1 and n is 1.

Particularly preferred are those compounds of formula I wherein
$R^1$ represents a methoxy group; most preferred are the following benzoylbenzenes:
6'-butoxy-2,6-dichloro-4',5'-dimethoxy-2'-methylbenzophenone (coded BB-1); 2,6-dichloro-4',5'-dimethoxy-6'-(2-fluorobenzyloxy)-2'-methylbenzophenone (coded BB-2); 6'-benzyloxy-4',5'-dimethoxy-2,6-dimethyl-2'-methylbenzophenone (coded BB-3); and 3-bromo-2',6-dimethyl-2,40 ,5',6'-tetramethoxybenzophenone (coded BB-4).

Preferred herbicides are the commercially available compounds selected from the group consisting of:
2,4-D, 2,4-DB, 2,4-DP, acetochlor, acifluorfen, alachlor, alloxydim, ametrydione, amidosulfuron, asulam, atrazin, azimsulfuron, benfuresate, bensulfuron, bentazon, bifenox, bromobutide, bromoxynil, butachlor, cafenstrole, carfentrazone, chloridazon, chlorimuron, chlorpropham, chlorsulfuron, chlortoluron, cinmethylin, cinosulfuron, clomazone, clopyralid, cyanazin, cycloate, cyclosulfamuron, cycloxydim, daimuron, desmedipham, di-methazone, dicamba, dichlobenil, diclofop, diflufenican, dimethenamid, dithiopyr, diuron, eptame, esprocarb, ethiozin, fenoxaprop, flamprop-M-isopropyl, flamprop-M-methyl fluazifop, fluometuron, fluoroglycofen, fluridone, fluroxypyr, flurtamone, fluthiamid, fomesafen, glufosinate, glyphosate, halosafen, haloxyfop, hexazinone, imazamethabenz, imazamethapyr, imazamox, imazapyr, imazaquin, imazethapyr, ioxynil, isoproturon, isoxaben, isoxaflutole, lactofen, MCPA, MCPP, mefenacet, metabenzthiazuron, metamitron, metazachlor, methyldimron, metolachlor, metribuzin, metsulfuron, molinate, nicosulfuron, norflurazon, oryzalin, oxadiargyl, oxasulfuron, oxyfluorfen, pendimethalin, picloram, pretilachlor, propachlor, propanil, prosulfocarb, pyrazosulfuron, pyridate, qinmerac, quinchlorac, quizalofopethyl, sethoxydim, simetryne, sulcotrione, sulfentrazone, sulfosate, terbutryne, terbutylazin, thiameturon, thifensulfuron, thiobencarb, tralkoxydim, triallate, triasulfuron, tribenuron, triclopyr, trifluralin.

Furthermore preferred are the derivatives of aryloxypicolineamides which are disclosed, for example, by European Patent Application EP-A-0 447 004, in particular, N-(4-fluorophenyl) 6-(3-trifluoromethylphenoxy)-pyrid-2-ylcarboxamide having the proposed common name picolinafen.

Examples of insecticidal compounds are alpha-cypermethrin, benfuracarb, BPMC, buprofezine, carbosulfan, cartap, chlorfenvinphos, chlorpyrifos-methyl, cycloprothrin, cypermethrin, esfenvalerate, ethofenprox, fenpropathrin, flucythrinate, flufenoxuron, hydramethylnon, imidacloprid, isoxathion, MEP, MPP, nitenpyram, PAP, permethrin, propaphos, pymetrozine, silafluofen, tebufenozide, teflubenzuron, temephos, terbufos, tetrachlorvinphos and triazamate.

Liquid active ingredients such as for example fenpropimorph can be formulated according to the present invention by adsorbing the active ingredient onto a carrier.

As a rule the non-aqueous SC according to the invention comprises by 50 to 400 g/L, preferably 75 to 375 g/L, in particular 80 to 350 g/L of one or more crop protection active compounds.

The adjuvants (b) are preferably selected from the group consisting of amine alkoxylates, alkylpolyglycosides, alkenyl succinic acid derivatives, polyvinylpyrrolidones, perfluoroalkyl acid derivatives, in particular perfluoro($C_{6-18}$) alkylphosphonic acids, perfluoro($C_{6-18}$)alkyl-phosphinic acids, perfluoro($C_{3-20}$)alkyl esters of polymeric carboxylic acids, mixtures thereof and mixtures with diluents.

The aliphatic moieties of the amines ethoxylates may be straight-chained or branched. Preferably these compounds correspond to a oligomer of the following formula

$H_{2n+1}C_n$—$N[(CH_2CH_2O)_xH]_2$, in which n is an integer from 9 to 20, in particular 12 to 18;

x is an integer from 2 to 14, in particular 2 to 10.

Of particular interest are those polyalkoxylated aliphatic amines, which are liquids at temperatures down to at least 20° C. having a viscosity of 100 to 1000 mPa·s at 25° C. The compounds which are commercially available under the trademark Berol® (Akzo-Nobel), in particular Berol® 381 has been proven to be especially advantageous.

The alkylpolyglycosides (APG) are obtainable from a acid-catalyzed Fischer reaction of starch or glucose syrups with fatty alcohols, in particular $C_{8-18}$ alcohols. Most preferred are $C_{8-10}$ and $C_{12-14}$ alkylpolyglycosides having a degree of polymerization of 1.3 to 1.6., in particular 1.4 or 1.5. These APGs are commercially available for example under the tradenames Agrimul® and Glucopon®, which are APGs diluted with water, in particular Glucopon® 215CSUP or Glucopon® 600CSUP from Henkel KGaA or Atplus®430, Atplus®435, Atplus®450, Atplus®469, which are APGs diluted with hydrotrope agents, from Uniqema (formerly ICI Surfactants).

Preferred polyoxyalkylene triglycerides are as a rule obtainable by alkoxylation of triglycerides. The alkoxylation of triglycerides results in mixtures of compounds with one to three glyceride side chains having 9–24, preferably 12–22 and in particular 14–20 C-atoms, in particular with ethyleneoxide. The aliphatic moieties of the said triglycerides may be straight-chained or branched. Preferably these compounds correspond to mixed oligomers resulting from the alkoxylation of castor or canola oil. Most preferred are castor and canola oil ethoxylate having 20 to 50, in particular 30 or 40 ethyleneoxide units, which are commercially available under the tradename Eumulgin®, in particular Eumulgin® RT40.

Preferred alkenyl succinic acid derivatives are compounds of formula

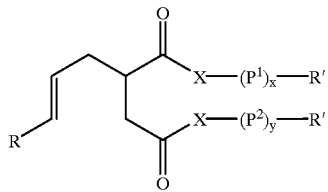

or salts thereof, in which

R represents a $C_{4-18}$ alkyl group, in particular a hexyl, heptyl or dodecyl group;

X represents O or $N(C_{1-6}$ alkyl)

$P^1$ and $P^2$ each represent a polymer back bone selected from the formulae (1) and(2):

—$CH_2$—$CH_2$—O— (1)

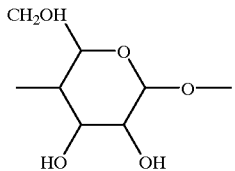
(2)

R' represents a hydrogen atom or an alkyl group, x represents 0 or an integer from 1 to 10, and y represents an integer from 1 to 10.

Preferred are alkenyl succinic acid diglucamides, alkenyl succinic acid alkoxylates and alkenyl succinic acid alkylpolyglykosides, in particular Atplus® ADG 1001 and Atplus® ADG 1201 obtainable from Uniqema.

Preferred polyvinylpyrrolidones (PVP) have an average molecular weight of more than 6000 g/mol, in particular 7000 to 9000 g/mol, most preferred is a PVP having an average molecular weight of 8000 g/mol which is available as Agrimer® 15 from ISP.

As a rule the aqueous SC according to the invention comprises 50 to 500 g/L, preferably 75 to 450 g/L, in particular 150 to 400 g/L of one or more adjuvants (b).

The non-ionic dispersants (c1) are preferably liquid polyalkoxylated aliphatic fatty acids or straight-chained alcohols. These adjuvants are as a rule obtainable by alkoxylation of fatty acids or straight-chained alcohols having 9–24, preferably 12–22 and in particular 14–20 C-atoms, with alkyleneoxide having 2–6, preferably 2–3 C-atoms, in particular with a mixture of ethylenoxide and propyleneoxide.

Preferably these compounds correspond to mixed random or block oligomers of the following formula

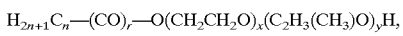

in which
r is 0 or 1, and the average of the indexes given is as follows:
n is an integer from 9 to 20, in particular 15 to 19;
x is an integer from 4 to 22, in particular 5 to 18; and
y is an integer from 6 to 12, in particular 7 to 10.

Of particular interest are those polyalkoxylated aliphatic alcohols, which are liquids at temperatures down to at least 20° C. having a viscosity of 30 to 100, in particular 50 to 80 mPa·s at 25° C. The compounds which are commercially available under the trademark Synperonic® (Uniqema), in particular Synperonic® 91-6.

In preferred embodiment of the present invention the non-ionic dispersant (c1) is a fatty acid or phenol. These dispersants are as a rule obtainable by alkoxylation fatty acids or phenols.

Preferred dipersants (c1) are for example Arkopal®-type alkylarylethoxylates (Clariant GmbH former Hoechst AG) or Genapol®-type (Clariant GmbH former Hoechst AG) alkanoylethoxylates.

Another preferred dispersant (c1) is a nonylphenolethoxylate for example Synperonic® NP-4, which is commercially available from Uniqema.

Furthermore preferred dispersants (c1) are are polyethyleneoxide-polypropyleneoxide block-copolymers of formula

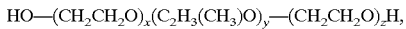

in which
the sum of x and z is an integer from 1 to 80, in particular 2 to 75; and
y is an integer from 10 to 70, in particular 20 to 60.

Most preferred are the Pluronic®-type block-copolymers, which are available from BASF AG, in particular Pluronic® PE. 10500.

As a rule the aqueous SC according to the invention comprises 5 to 75 g/L, preferably 7.5 to 40 g/L, in particular 8 to 30 g/L of one or more non-ionic dispersants (c1).

The anionic dispersant (c2) is as a rule an alkali or earth alkali sulfonate, which includes also concentrated mixtures of such an alkali or earth alkali sulfonate with a polar diluent such as an alcohol an aromatic hydrocarbon, preferably butanol, 2-ethylhexanol or Solvesso® 200. Such a mixture preferably consists of 40 to 90 wt.-% of at least one alkali or earth alkali sulfonate and 10 to 60 wt.-% of an organic diluent. Ammonium, alkali and earth alkali alkylbenzene sulfonates are preferred, in particular calcium dodecylbenzene sulfonates such as Rhodocal® 70/B (Rhodia, formerly Rhône-Poulenc) or Phenylsulfonat CA100 (Clariant GmbH, formerly Hoechst AG) or isopropylammonium dodecyl benzene sulfonate such as Atlox® 3300B (Uniqema). In particularly preferred embodiment of this invention the anionic dispersant is an alkylnaphthalene sulfonic acid formaldehyde condensate such as Morwet® D425 (Witco Corporation, USA).

As a rule the aqueous SC according to the invention comprises 10 to 100 g/L, preferably 10 to 80 g/L, in particular 15 to 75 g/L of one or more anionic dispersants.

The appropriate relative amounts of active ingredient (a) and the adjuvant (b) lie, in accordance with the invention, between 1:0.5 and 1:100, preferably between 1:0.75 and 1:10 and, in particular, between 1:1 and 1:5. In general and within certain limits, the pesticidal efficacy can be enhanced to a higher degree by the addition of larger amounts of the adjuvant (b) as is shown in the experimental results described below.

Recommended doses for various applications are known for the crop protection active compounds (a) where the efficacy can be enhanced in accordance with the invention. Addition of the adjuvants suggested here can (depending on the active ingredient, the adjuvant and their amounts) reduce the amount of active ingredient per hectare required in these recommendations by half or more, whereby it becomes possible to control additional diseases at reasonable doses.

An important advantage is the rapid onset and the high persistency of activity on use of the new additives. This enlarges the period for application of the pesticide and makes its use more flexible.

The pesticidal formulations according to the present invention can be used protectively and curatively.

As a rule the aqueous SC according to the invention comprises 200 to 800 g/L, preferably 300 to 700 g/L, in particular 350 to 650 g/L of water.

In a particularly preferred embodiment according to this invention the non-aqueous SC essentially consists of (a) 75 to 350 g/L, preferably 100 to 300 g/L of one or more crop protection active compounds, in particular a compound of formula I;

(b) 75 to 450 g/L, preferably 100 to 300 g/L of one or more adjuvants selected from the group consisting of alkoxylated amines, alkylpolyglycosides and alkenyl succinic anhydride diglucamides.

(c) at least one surfactant selected from the groups (c1) and (c2):
 (c1) 5 to 25 g/L, preferably 7.5 to 20 g/L of one or more non-ionic dispersant;
 (c2) 10 to 50 g/L, preferably 15 to 40 g/L of one or more anionic dispersant;

(d) 0 to 75 g/L, preferably 0.5 to 60 g/L of an anti-freezing agent;

(e) 0 to 5 g/L, preferably 0.5 to 5 g/L of a defoamer;

(f) up to 10 g/L, preferably 0.5 to 5 g/L of one or more preservatives, (g) 300 to 700 g/L water, and (h) up to 30 g/L, preferably 0.5 to 15 g/L of one or more structure agents, preferably Xanthan gum such as Rhodopol® 23 from Rhodia and/or hydrated silicates such as Attagel® 50 from Engelhard Corp. or Veegum® T from Vanderbilt Export Corp.

The adjuvants (b) according to the invention, the pesticidal active compounds (a) and dispersants (c) and water and optionally one or more anti-freezing agents (d) and/or defoamers are processed to suspension concentrates according to the invention by well-established procedures. These procedures include intensive mixing and/or milling of the active ingredients with the other substances, such as solvents, wetting agents, and adjuvants. The form of application such as spraying, atomizing, dispersing or pouring may be chosen like the compositions according to the desired objectives and the given circumstances.

Suspension concentrates according to the present invention are usually produced so as to obtain a stable, non-sedimenting flowable product and usually contain 5 to 40% w/v active ingredient, 5 to 50% w/v adjuvant, 0.5 to 17.5% w/v of dispersing agents, 0 to 15% w/v antifreezing agent, 0 to 10% w/v of suspending agents such as protective colloids and thixotropic agents, 0 to 2.5% w/v preservatives, 0 to 10% w/v of other additives such as defoamers, corrosion inhibitors, stabilizers, penetrants and stickers, and an organic liquid in which the active ingredient is substantially insoluble.

Preferred anti-foam agents (e) are silica, polydialkylsiloxanes and mixtures thereof, in particular Rhodorsil® 416, Rhodorsil® 426R or Rhodosil® 454 from Rhodia. Particularly preferred is a combination of polydimethylsiloxanes and perfluoroalkylphosphonic/perfluoroalkylphosphinc acids.

The term preservatives (f) includes chemical stabilizers to prevent decomposition of the compound of formula I during storage such as alkaline earth and transition metal sulfates and biocides, in particular bactericides such as Proxel® GXL (Zeneca)

In a preferred embodiment the crop protection compound (a) is air-milled optionally in the presence of dispersant (c2) before admixing the components (b) to (g) and optionally (h).

The finished non-aqueous suspension concentrates according to the invention are stable in storage, i.e. even on storage over a relatively long period. Although phase separation may occur upon storage due to sedimentation of the active ingredient, no aggregates are formed. The SCs according to the present invention allow the inclusion of high loadings of one or more adjuvants in a one-pack formulation with a pesticide and, therefore, offer the advantage of an optimized and easy-to-use formulation of the crop protection active compound. The separate addition of an adjuvant by the end-user before application has therefore become unnecessary.

Aqueous dispersions and emulsions, for example compositions obtained by diluting the formulated product according to the invention with water, also lie within the scope of the invention.

As a commodity the compositions may preferably be in a concentrated form whereas the end user generally employs diluted compositions. The compositions may be diluted to a concentration down to 0.001% of active ingredient. The doses are usually in the range of 0.01 to 10 kg a.i./ha.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

Examples of aqueous suspension concentrates according to the invention are shown in the following examples A to M:

Identity of Ingredients Used in Examples

| Name | Function | Identity |
| --- | --- | --- |
| Agrimer 15 (ISP) | Adjuvant | Polyvinylpyrrolidone having a molecular weight of 8,000 g/mol |
| Agrimer 30 (ISP) | Adjuvant | Polyvinylpyrrolidone having a molecular weight of 38,000 g/mol |
| Agrimer VA7W (ISP) | Adjuvant | Polyvinylacetate polyvinylpyrrolidone copolymer |
| Agsol EX 8 (ISP) | Adjuvant | N-octylpyrrolidone |
| Arkopal N-80 (Clariant) | Adjuvant | Nonylphenol polyglycolether (8 EO) |
| Atplus 450 ® (Uniqema) | Adjuvant | Alkylpolysaccharide blend |
| Atplus 469 ® (Uniqema) | Adjuvant | Alkylpolysaccharide blend |
| Atplus 430 ® (Uniqema) | Adjuvant | Alkylpolysaccharide blend |
| Atplus 435 ® (Uniqema) | Adjuvant | Alkylpolysaccharide blend |
| Atplus MBA 11-7 ® (Uniqema) | Adjuvant | branched alcohol ethoxylate |
| Berol 381 (Akzo-Nobel) | Adjuvant | Amine ethoxylate |
| Bevaloid 6338 (Rhodia) | Defoamer | Emulsion of inert polymeric substances |
| Eumulgin RT40 (Henkel) | Adjuvant | Castor oil ethoxylate (40 EO) |
| Fluorad FC-430 (3M) | Adjuvant | Perfluoroaliphatic polymeric ester |
| Fluorad FC-129 (3M) | Adjuvant | Perfluoroalkylsulfonate |
| Fluowet PL80 (Clariant) | Adjuvant | 80% mixture of perfluorinated alkylphosphinic/alkylphosphonic acids |
| Geropon T36 (Rhodia) | Dispersant | Sodium polycarboxylate |
| Glucopon 600CSUP (Henkel) | Adjuvant | $C_{12-14}$ alkylpolyglycoside in water |
| Glucopon 215CSUP (Henkel) | Adjuvant | $C_{8-10}$ alkylpolyglycoside in water |
| Morwet D425 (Witco) | Dispersant | Alkylnaphthalene sulfonic acid formaldehyde condensate |
| Pluronic PE10500 (BASF) | Dispersant | Ethyleneoxide/propyleneoxide block copolymer |
| Proxel GXL (Zeneca) | Biocide | aqueous dipropylene glycol solution containing 20% 1,2-benzisothiazoli-3-one |
| Rhodopol 23 (Rhodia) | Structure agent | heteropolysccharide having a molecular weight of about 2,000,000 g/mol |
| Atplus ADG 1001 (Uniqema) | Adjuvant | $C_{12}$ alkenyl succinic anhydride diglucamide |
| Atplus ADG 1201 (Uniqema) | Adjuvant | 50% $C_{12}$ alkenyl succinic anhydride diglucamide in propylene glycol |
| Silicon Antifoam TP 20 (OSi Specialities GmbH) | Defoamer | Polydimethylsiloxane emulsion |
| Silica FK 320 (Degussa AG) | Defoamer | Amorphous silica |
| Rhodorsil 426 R (Rhodia) | Defoamer | polydimethylsiloxane emulsion |
| Soprophor FL (Rhodia) | Dispersant | Ammonium polyarylphenyl ether phosphate |
| Supragil MNS/90 (Rhodia) | Dispersant | Sodium naphthalene sulfonate formaldehyde condensate |
| Vanisperse CB (Lignotech, Norway) | Dispersant | Sodium ligninsulfonate |
| Veegum T (Vanderbilt Exp. Corp., USA) | Structure agent | Hydrated magnesium aluminium silicate |
| Synperonic 91-6 (Uniqema) | Adjuvant | alcohol ethoxylate |

EXAMPLES 1 to 3

The following SC formulations according to the invention are prepared by mixing the ingredients with the exception of the structure agent, the antifreeze agent and the adjuvant in a dissolver. Subsequently, the suspension is milled using a Dyno-mill. The adjuvant is then stirred into the milled suspension. Subsequently, a suspension of the structure agent and the antifreeze agent is produced and also stirred into the milled suspension.

Alternatively, the structure agent can be added to the un-milled suspension and milled together with the active ingredient.

The obtained SC formulations are compared with similar SC formulations (C-1 and C-2), in which the adjuvant (b) was replaced by n-octylpyrrolidone or an alcohol ethoxylate (Synperonic 91-6)

The following formulations are obtained:

| | Concentration (g/L) Example | | | | |
|---|---|---|---|---|---|
| Ingredient | 1 | 2 | 3 | C-1 | C-2 |
| BB-4 | 200 | 200 | 200 | 200 | 200 |
| Morwet D425 | 20 | 20 | 20 | 20 | 20 |
| Pluronic PE 10500 | 10 | 10 | 10 | 10 | 10 |
| Proxel GXL | 2 | 2 | 2 | 2 | 2 |
| Rhodorsil 426R | 2 | 2 | 2 | 2 | 2 |
| Rhodopol 23 | 3 | 3 | 3 | 3 | 3 |
| Propylene glycol | 50 | 50 | 50 | 50 | 50 |
| Agsol Ex8 | — | — | — | 50 | — |
| Synperonic 91-6 | — | — | — | 200 | 250 |
| Atplus 450 | 250 | — | — | — | — |
| Atplus 469 | — | 250 | — | — | — |
| Atplus ADG 1201 | — | — | 250 | — | — |
| Water | to 1L | to 1L | to 1L | to 1L | to 1L |

The density, and the particle size distribution upon storage for two weeks at room temperature (RT), at 40° C. (2W40° C.) and at 54° C. (2W54° C.) of the SC formulations are shown in the following table I:

TABLE I

| | | Example | | | | |
|---|---|---|---|---|---|---|
| Properties | | 1 | 2 | 3 | C-1 | C-2 |
| Density | [g/mL] | 1.106 | 1.121 | 1.116 | 1.078 | 1.085 |
| Particle size | $x_{10}$ [μm] | 0.74 | 0.74 | 0.76 | 0.88 | 0.74 |
| distribution | $x_{50}$ [μm] | 1.92 | 1.92 | 1.98 | 3.19 | 1.95 |
| (RT) | $x_{90}$ [μm] | 4.83 | 4.78 | 5.00 | 6.77 | 4.77 |
| Particle size | $x_{10}$ [μm] | 0.73 | 0.74 | 0.73 | 1.04 | 0.82 |
| distribution | $x_{50}$ [μm] | 1.87 | 1.88 | 1.89 | 3.73 | 2.28 |
| (2W40 ° C.) | $x_{90}$ [μm] | 4.56 | 4.50 | 4.70 | 7.59 | 5.44 |
| Particle size | $x_{10}$ [μm] | 0.74 | 0.76 | 0.74 | 1.39 | 1.00 |
| distribution | $x_{50}$ [μm] | 1.90 | 1.96 | 1.88 | 5.07 | 2.89 |
| (2W54 ° C.) | $x_{90}$ [μm] | 4.51 | 4.42 | 4.49 | 10.16 | 6.54 |

Whereas the particle size distribution of the formulations according to the present invention is constant upon storage at elevated temperature, the particle size increases drastically with alcohol ethoxylates as adjuvants alone or with an N-alkylpyrrolidone.

EXAMPLES 4 to 6

The following SC formulations according to the invention are prepared analogously to examples 1 to 3.

The following formulations are obtained:

| | Concentration (g/L) Example | | |
|---|---|---|---|
| Ingredient | 4 | 5 | 6 |
| BB-4 | 200 | 200 | 200 |
| Morwet D425 | 20 | 20 | 20 |
| Pluronic PE 10500 | 10 | 10 | 10 |
| Proxel GXL | 2 | 2 | 2 |
| Rhodorsil 426R | 2 | 2 | 2 |
| Rhodopol 23 | 3 | 3 | 3 |
| Propylene glycol | 50 | 50 | 50 |
| Agrimer 15 | 250 | — | — |
| Fluowet PL80 | — | 70 | — |
| Atplus 430 | — | — | 250 |
| Water | to 1L | to 1L | to 1L |

The density, and the particle size distribution upon storage for two weeks at room temperature (RT), at 40° C. (2W40° C.) and at 54° C. (2W54° C.) of the SC formulations are shown in the following table II:

TABLE II

| | | Example | | |
|---|---|---|---|---|
| Properties | | 4 | 5 | 6 |
| Density | [g/mL] | 1.141 | 1.100 | 1.121 |
| Particle size | $x_{10}$ [μm] | 0.75 | 0.76 | 0.75 |
| distribution | $x_{50}$ [μm] | 1.98 | 2.04 | 1.95 |
| (RT) | $x_{90}$ [μm] | 4.98 | 5.39 | 4.02 |
| Particle size | $x_{10}$ [μm] | 0.73 | 0.76 | 0.74 |
| distribution | $x_{50}$ [μm] | 1.86 | 2.03 | 1.90 |
| (2W40 0° C.) | $x_{90}$ [μm] | 4.55 | 5.26 | 4.09 |
| Particle size | $x_{10}$ [μm] | 0.75 | 0.75 | 0.75 |
| distribution | $x_{50}$ [μm] | 1.92 | 2.03 | 1.95 |
| (2W54 ° C.) | $x_{90}$ [μm] | 4.55 | 5.38 | 4.01 |

The particle size distribution of the formulations according to the present invention is constant upon storage at elevated temperature.

EXAMPLE 7

The following SC formulation according to the invention is prepared analogously to Examples 1 to 3. It is compared with a similar SC formulation (C-3), in which the adjuvant (b) was replaced by a polyoxyethylene sorbitol ester (Tween 80).

The following formulations are obtained:

| | Concentration (g/L) Example | |
|---|---|---|
| Ingredient | 7 | C-3 |
| BB-4 | 200 | 200 |
| Morwet D425 | 20 | 20 |
| Pluronic PE 10500 | 10 | 10 |
| Proxel GXL | 2 | 2 |
| Rhodorsil 426R | 2 | 2 |
| Rhodopol 23 | 3 | 3 |
| Propylene glycol | 50 | 50 |
| Atplus 435 | 250 | — |
| Tween 80 | — | 250 |
| Water | to 1L | to 1L |

The density, and the particle size distribution upon storage at room for two weeks at temperature (RT), 2 at 40° C. (2W40° C.) and at 54° C. (2W54° C.) of the SC formulations are shown in the following table III:

TABLE III

| Properties | | Example 7 | C-3 |
|---|---|---|---|
| Density | [g/mL] | 1.111 | 1.108 |
| Particle size | $x_{10}$ [μm] | 0.75 | 0.75 |
| distribution | $x_{50}$ [μm] | 1.97 | 2.27 |
| (RT) | $x_{90}$ [μm] | 4.97 | 4.64 |
| Particle size | $x_{10}$ [μm] | 0.74 | 0.84 |
| distribution | $x_{50}$ [μm] | 1.89 | 2.27 |
| (2W40° C.) | $x_{90}$ [μm] | 4.54 | 5.40 |
| Particle size | $x_{10}$ [μm] | 0.76 | 0.98 |
| distribution | $x_{50}$ [μm] | 1.96 | 2.74 |
| (2W54° C.) | $x_{90}$ [μm] | 4.64 | 6.26 |

Whereas the particle size distribution of the formulations according to the present invention is constant upon storage at elevated temperature, the particle size increases drastically with polyoxyethylene sorbitol esters as adjuvants.

EXAMPLES 8 to 12

The following SC formulations according to the invention are prepared analogously to Examples 1 to 3.

The following formulations are obtained:

| | Concentration (g/L) Example | | | | |
|---|---|---|---|---|---|
| Ingredient | 8 | 9 | 10 | 11 | 12 |
| BB-4 | 200 | 200 | 200 | 200 | 200 |
| Morwet D425 | 20 | 20 | 20 | 20 | 20 |
| Pluronic PE 10500 | 10 | 10 | 10 | 10 | 10 |
| Proxel GXL | 2 | 2 | 2 | 2 | 2 |
| Rhodorsil 426R | 2 | 2 | 2 | 2 | 2 |
| Rhodopol 23 | 3 | 3 | 3 | 3 | 3 |
| Propylene glycol | 50 | 50 | 50 | 50 | 50 |
| Berol 381 | 250 | — | — | — | — |
| Fluorad FC430 | — | 100 | — | — | — |
| Fluorad FC129 | — | — | 100 | — | — |
| Glucopon 600 CSUP | — | — | — | 250 | — |
| Glucopon 215 CSUP | — | — | — | — | 250 |
| Water | to 1L | to 1L | to 1L | to1L | to 1L |

The density, and the particle size distribution upon storage for two weeks at room temperature (RT) and at 54° C. (2W54° C.) of the SC formulations are shown in the following table IV:

TABLE IV

| Properties | | Example 8 | 9 | 10 | 11 | 12 |
|---|---|---|---|---|---|---|
| Density | [g/mL] | 1.101 | 1.105 | 1.101 | 1.103 | 1.085 |
| Particle size | $x_{10}$ [μm] | 0.72 | 0.74 | 0.73 | 0.73 | 0.74 |
| distribution | $x_{50}$ [μm] | 1.97 | 1.96 | 1.96 | 2.05 | 2.05 |
| (RT) | $x_{90}$ [μm] | 5.35 | 5.50 | 5.52 | 5.85 | 5.78 |
| Particle size | $x_{10}$ [μm] | 0.70 | 0.70 | 0.71 | 0.72 | 0.72 |
| distribution | $x_{50}$ [μm] | 1.87 | 1.84 | 1.84 | 1.96 | 1.92 |
| (2W54° C.) | $x_{90}$ [μm] | 5.12 | 5.01 | 5.00 | 5.57 | 5.30 |

The particle size distribution of the formulations according to the present invention is constant upon storage at elevated temperature.

EXAMPLES 13 to 15

The following SC formulations according to the invention are prepared analogously to Examples 1 to 3

The following formulations are obtained:

| | Concentration (g/L) Example | | |
|---|---|---|---|
| Ingredient | 13 | 14 | 15 |
| BB-4 | 200 | 200 | 200 |
| Morwet D425 | 20 | 20 | 20 |
| Pluronic PE 10500 | 10 | 10 | 10 |
| Proxel GXL | 2 | 2 | 2 |
| Rhodorsil 426R | 2 | 2 | 2 |
| Rhodopol 23 | 3 | 3 | 3 |
| Propylene glycol | 50 | 50 | 50 |
| SCS 3631 | 250 | — | — |
| Emulgin RT40 | — | 250 | — |
| Agrimer 30 | — | — | 100 |
| Water | to1L | to 1L | to1L |

The density, and the particle size distribution upon storage for two weeks at room temperature (RT) and 2 weeks at 54° C. (2W54° C.) of the SC formulations are shown in the following table V:

TABLE V

| Properties | | Example 13 | 14 | 15 |
|---|---|---|---|---|
| Density | [g/mL] | 1.126 | 1.107 | 1.104 |
| Particle size | $x_{10}$ [μm] | 0.72 | 0.72 | 0.73 |
| distribution | $x_{50}$ [μm] | 2.03 | 1.95 | 2.98 |
| (RT) | $x_{90}$ [μm] | 5.77 | 5.44 | 5.50 |
| Particle size | $x_{10}$ [μm] | 0.70 | 0.71 | 0.70 |
| distribution | $x_{50}$ [μm] | 1.88 | 1.91 | 1.84 |
| (2W54° C.) | $x_{90}$ [μm] | 5.14 | 5.45 | 4.96 |

The particle size distribution of the formulations according to the present invention is constant upon storage at elevated temperature.

EXAMPLES 16 to 18

The following SC formulations according to the invention are prepared analogously to Examples 1 to 3.

| | Concentration (g/L) | | |
|---|---|---|---|
| Ingredient | Example 16 | Example 17 | Example 18 |
| Dimethomorph | 375 | 375 | 250 |
| Soprophor FL | 15.6 | 15.6 | 7.8 |
| Bevaloid 6338 | 1.9 | 1.9 | 1.3 |
| Proxel GXL | 0.9 | 0.9 | 0.7 |
| Propylene glycol | 50 | 50 | 33 |
| Rhodopol 23 | 1.7 | 1.7 | 1.1 |
| Fluowet PL80 | 250 | — | — |
| Atplus 469 | — | 250 | — |
| Glucopon 215 CSUP | — | — | 500 |
| Water | to 1liter | to 1 liter | to 1 liter |
| Density (g/mL) | 1.16 | 1.15 | 1.12 |

EXAMPLES 19 to 21

The following SC formulations according to the invention are prepared analogously to Examples 1 to 3.

| Ingredient | Concentration (g/L) Example 19 | Example 20 | Example 21 |
|---|---|---|---|
| Metconazole | 100 | 100 | 100 |
| Vanisperse CB | 13.3 | 13.3 | 13.3 |
| Rhodorsil 426R | 0.6 | 0.6 | 0.6 |
| Proxel GXL | 0.8 | 0.8 | 0.8 |
| Propylene glycol | 64 | 64 | 64 |
| Rhodopol 23 | 1.4 | 1.4 | 1.4 |
| SCS 3631 | 100 | — | — |
| Atplus 469 | — | 100 | — |
| Glucopon 215 CSUP | — | — | 100 |
| Water | to 1liter | to 1liter | to 1liter |
| Density (g/mL) | 1.11 | 1.09 | 1.08 |

EXAMPLES 22 to 24

The following SC formulations according to the invention are prepared analogously to Examples 1 to 3.

| Ingredient | Concentration (g/L) Example 22 | Example 23 | Example 24 |
|---|---|---|---|
| Picolinafen | 125 | 150 | 125 |
| Supragil MNS/90 | 7.5 | 9 | 7.5 |
| Geropon T36 | 6.3 | 7.5 | 6.3 |
| Rhodorsil 426R | 0.5 | 0.6 | 0.5 |
| Proxel GXL | 0.3 | 0.3 | 0.3 |
| Citric Acid | 3.0 | 3.6 | 3.0 |
| Propylene glycol | 25 | 30 | 25 |
| Rhodopol 23 | 1.25 | 1.5 | 1.25 |
| Agrimer VA7W | 500 | — | — |
| Atplus 469 | — | 400 | — |
| Glucopon 215 CSUP | — | — | 500 |
| Water | to 1 liter | to 1liter | to 1 liter |
| Density (g/mL) | 1.10 | 1.11 | 1.07 |

EXAMPLE 25

The following SC formulation according to the invention is prepared analogously to Examples 1 to 3

| Ingredient | Concentration (g/L) |
|---|---|
| Pendimethalin | 300 |
| Agrimer 15 | 250 |
| Soprophor FL | 45 |
| Arkopal N-80 | 38 |
| Veegum T | 4.5 |
| Silicon Antifoam TP 20 | 5.6 |
| Proxel GXL | 0.75 |
| Silica FK 320 | 3.8 |
| Water | to 1 liter |
| Density (g/mL) | 1.13 |

The SCs described in the examples 16–25 show insignificant particle growth when stored for 2 weeks at 54° C. (2 weeks at 40° C. for example 28). When the adjuvant is replaced by the equivalent amount of alcohol ethoxylate (e.g. Synperonic 91-6), unacceptable particle growth is observed in all cases.

What is claimed is:

1. A method for the enhancement of the efficacy of crop protection active compounds which comprises combining said crop protection active compounds with an effective amount of at least one adjuvant, which has the capability of reducing the surface tension in an aqueous spray dilution to 40 mN/m or lower being selected from the group consisting of amine alkoxylates, polyoxyalkylene triglycerides, alkylpolyglycosides, alkenyl succinic anhydride derivatives, polyvinylpyrrolidones, perfluoroalkyl acids derivatives, and mixtures thereof.

2. An aqueous, concentrated suspension (SC) for crop protection active compounds which comprises (a) 50 to 400 g/L of at least one crop protection active compound;

(b) 50 to 500 g/L of at least one adjuvant, which has the capability of reducing the surface tension in the spray dilution to 40 mN/m or lower and does not promote the particle growth of the crop protection active compound;

(c) at least one surfactant selected from the groups (c1) and (c2):

(c1) 5 to 75 g/L of one or more non-ionic dispersants, and (c2) 10 to 100 g/L of one or more anionic dispersants, (d) up to 150 g/L of one or more anti-freezing agents, (e) up to 25 g/L of one or more defoamers, (f) up to 25 g/L of one or more preservatives, and (g) 200 to 800 g/L of water, wherein the adjuvant (b) is selected from the group consisting of amine alkoxylates, polyoxyalkylene triglycerides, alkylpolyglycosides, alkenyl succinic anhydride derivatives, polyvinylpyrrolidones, perfluoroalkyl acids derivatives, and mixtures thereof.

3. A SC in accordance with claim 2 wherein the crop protection active compound (a) comprises a benzoylbenzene of formula I (I)

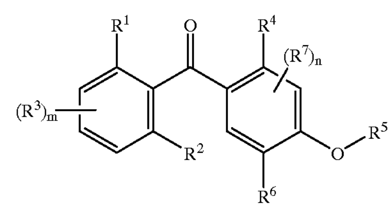

wherein $R^1$ represents a halogen atom, an optionally substituted alkyl, alkanoyloxy or alkoxy group; or a hydroxy group, $R^2$ represents a halogen atom, an optionally substituted alkyl group, $R^3$ represents a halogen atom or an optionally substituted alkyl group, m is 0 or an integer of 1 to 3;

$R^4$ independently represents a halogen atom, an optionally substituted alkyl or alkoxy group or a nitro group;

$R^5$ represents an optionally substituted alkyl group;

$R^6$ represents a halogen atom, a cyano, carboxy, hydroxy or nitro group or an optionally substituted alkyl, alkoxy, alkenyl, alkylthio, alkylsulphinyl, alkylsulphonyl or amino group;

R[7] represents a halogen atom or a nitro group, an optionally substituted alkyl, alkoxy, alkenyloxy, alkynyloxy, alkylthio, cycloalkyl, cycloalkyloxy, aryloxy group; and n is 0, 1 or 2.

4. A SC in accordance with claim 2 comprising 75 to 450 g/L of at least one alkylpolyglycoside, at least one amine ethoxylate or at least one alkenyl succinic anhydride diglucamide.

5. A SC in accordance with claim 1 comprising 55 to 150 g/L of at least one perfluoro($C_{6-18}$)alkylphosphonic acid, perfluoro($C_{6-18}$)alkylphosphinic acid or a mixture thereof.

6. A SC in accordance with claim 2 wherein the ratio of the crop protection active compounds (a) to said adjuvant (b) is between 1:05 and 1:100, preferably between 1:0.75 and 1:10.

7. A SC in accordance with claim 2 comprising in addition to the components (a) to (g):

(h) 0.1 to 30 g/l of at least one thickener.

8. A SC in accordance with claim 2 wherein the non-ionic dispersant (c1) is a block copolymer which consists of a polyoxypropylene and polyoxyethylene moieties.

9. A SC in accordance with claim 2 wherein the anionic dispersant (c2) is an amino sulfonate or an alkali or earth alkali sulfonate.

10. A SC in accordance with claim 2 wherein the anti-freezing agent (d) is an alkyleneglycol derivative.

11. A SC in accordance with claim 2 wherein the defoamer (e) is a silicone derivative.

12. A method for combating a fungus at a locus which comprises diluting a formulation as claimed in any of the claims 2 to 11 with water and treating said locus with the obtained diluted aqueous formulation.

* * * * *

UNITED STATES PATENT AND TRADEMARK OFFICE
CERTIFICATE OF CORRECTION

PATENT NO. : 6,383,984 B1
DATED : May 7, 2002
INVENTOR(S) : Michael Aven

It is certified that error appears in the above-identified patent and that said Letters Patent is hereby corrected as shown below:

<u>Column 17,</u>
Line 10, "claim 1" should be -- claim 2 --.
Line 15, "1:05" should be -- 1:0.5 --.

Signed and Sealed this

Twenty-fifth Day of June, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,383,984 B1
DATED : May 7, 2002
INVENTOR(S) : Michael Aven

It is certified that error appears in the above-identified patent and that said Letters Patent is hereby corrected as shown below:

<u>Column 4,</u>
Line 47, "3-bromo-2',6-" should be -- 5-bromo-2',6- --.

Signed and Sealed this

Nineteenth Day of August, 2003

JAMES E. ROGAN
*Director of the United States Patent and Trademark Office*